(12) United States Patent
De Leeuw et al.

(10) Patent No.: US 8,796,323 B2
(45) Date of Patent: Aug. 5, 2014

(54) DEFENSIN-LIKE MOLECULES AS NOVEL ANTIMICROBIAL AGENTS

(75) Inventors: Erik De Leeuw, Baltimore, MD (US); Alexander D. MacKerell, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 13/883,564

(22) PCT Filed: Nov. 4, 2011

(86) PCT No.: PCT/US2011/059432
§ 371 (c)(1),
(2), (4) Date: May 3, 2013

(87) PCT Pub. No.: WO2012/061767
PCT Pub. Date: May 10, 2012

(65) Prior Publication Data
US 2013/0231376 A1  Sep. 5, 2013

Related U.S. Application Data

(60) Provisional application No. 61/410,112, filed on Nov. 4, 2010.

(51) Int. Cl.
*A01N 43/78* (2006.01)
*A61K 31/425* (2006.01)

(52) U.S. Cl.
USPC ........................................................ 514/367

(58) Field of Classification Search
None
See application file for complete search history.

(56) References Cited

U.S. PATENT DOCUMENTS

| 4,840,784 A | 6/1989 | Frank |
| 6,399,370 B1 * | 6/2002 | Wilson et al. ................. 435/325 |
| 2003/0013836 A1 | 1/2003 | Takanishi |
| 2003/0092685 A1 | 5/2003 | Nitz |
| 2004/0137482 A1 | 7/2004 | Eckert |

OTHER PUBLICATIONS

Rurack et al., Chemical Physics Letters, 2000, 320, 87-94.*
Fighting the Impact of Antibiotic-Resistant Bacteria, FDA Consumer Health Information, 2013.*
Wang et al. (Phys. Chem. Chem. Phys., 2004, 6, 3437-3446).*
Garcia-Acosta et al. (Chem. Commun., 2006, 2239-2241).*
Reb Lai et al., "Two novel non-cationic defensin-like antimicrobial peptides from haemolymph of the female tick, *Amblymomma hebraeum*", Biochemical Journal, 2004, vol. 379, pp. 681-685, see p. 681.
International Search Report in related application PCT/US2011/059432.
Written Opinion in related application PCT/US2011/059432.
International Preliminary Report on Patentability in related application PCT/US2011/059432.
See also co-pending related U.S. Appl. No. 13/911,234.

* cited by examiner

*Primary Examiner* — Dennis Heyer
*Assistant Examiner* — Daniel M Podgorski
(74) *Attorney, Agent, or Firm* — Kristina Castellano; Castellano P.L.L.C.

(57) ABSTRACT

Disclosed are methods of treating and/or preventing infections in mammals caused by microorganisms, by administering to a mammal a therapeutically effective amount of at least one defensin-like molecule, e.g., in a composition that includes such molecule. Also disclosed are the use of such defensin-like molecules for treating and/or preventing infections in mammals; and kits that may include such molecules, or compositions that include such molecules, as well as instructions for using such molecules to treat a mammal.

6 Claims, 13 Drawing Sheets

Cmpd #1 (5107930)

Cmpd #2 (5100015)  Cmpd #4 (7771-0701)

Cmpd #3 (1499-1221)  Cmpd #5 (0251-0215)

| Structure | ID | Mol. Weight | Mol. Name |
|---|---|---|---|
| 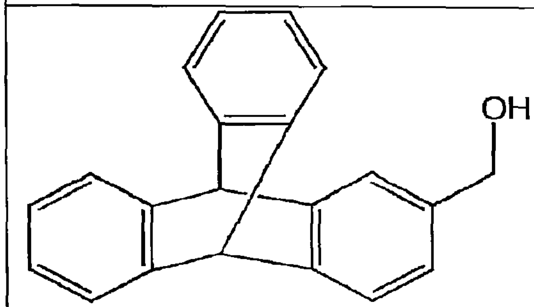 | 5100015 | 284.4 | Pentacyclo[6.6.6.0~2,7~.0~9,14~.0~15,20~]icocose-2,4,6,9,11,13,15,17,19-nonaen-4-ylmethanol |
| 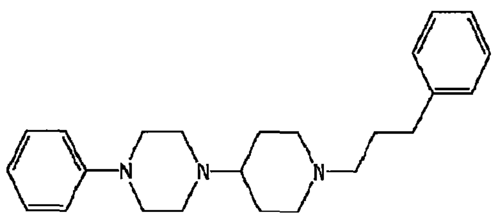 | 6785396 | 453.6 | 1-phenyl-4-[1-(3-phenylpropyl)-4-piperidinyl]piperazine |
| 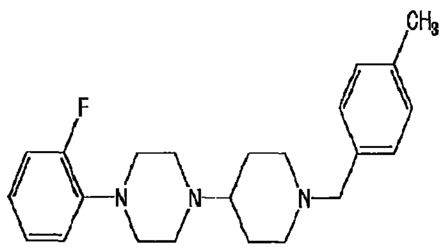 | 6711103 | 367.5 | 1-(2-fluorophenyl)-4-[1-(4-methylbenzyl)-4-piperidinyl]piperazine |

FIG. 9 (cont.)

| Structure | ID | MW | Name |
|---|---|---|---|
| 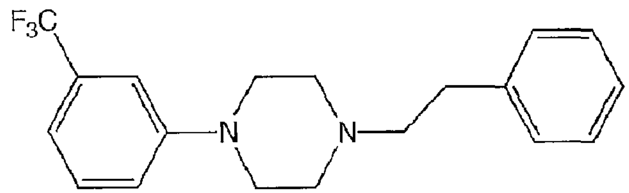 | 5422765 | 334.4 | 1-(2-phenylethyl)-4-[3-(trifluoromethyl)phenyl]piperazine |
| 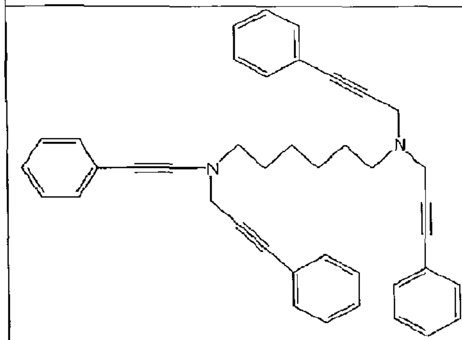 | 5230300 | 645.7 | N,N,N',N'-tetrakis(3-phenyl-2-propyn-1-yl)-1,6-hexanediamine dihydrochloride |
| 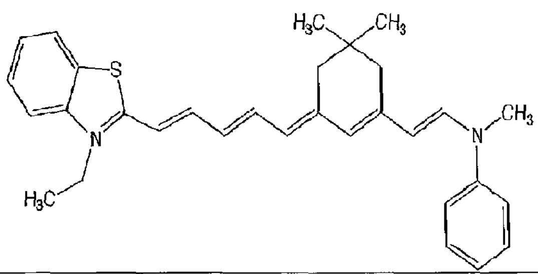 | 5107930 | 568.6 | 2-[3-(5,5-dimethyl-3-(2-[methyl(phenyl)amino]vinyl)-2-cyclohexen-1-ylidene)-1-propen-1-yl]-3-ethyl-1,3-benzothiazol-3-ium iodide |

| Structure | Formula Structure | Mol. Weight | ID Number |
|---|---|---|---|
| 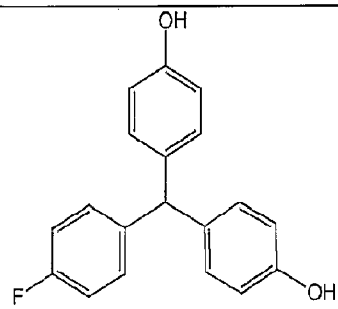 | $C_{19}H_{15}FO_2$ | 294.32 | 0251-0215 |
| 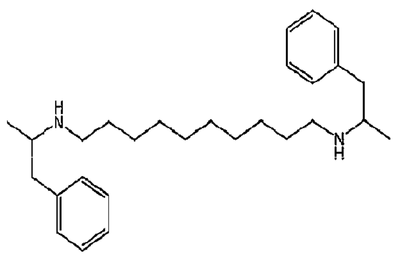 | $C_{28}H_{44}N_2$ | 408.66 | 8006-3639 |
| 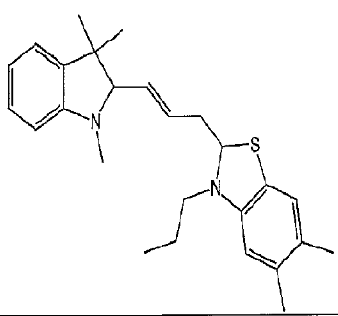 | $C_{26}H_{34}N_2S$ | 406.63 | 7771-0701 |
| 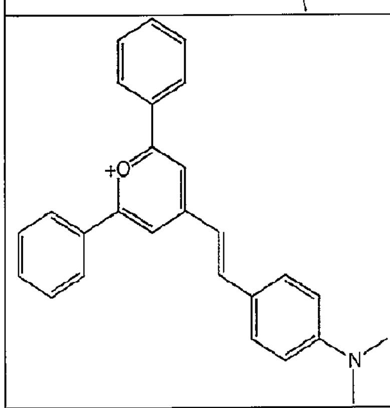 | $C_{27}H_{24}NO^+$ | 378.49 | 1499-1221 |

…

DEFENSIN-LIKE MOLECULES AS NOVEL ANTIMICROBIAL AGENTS

STATEMENT REGARDING FEDERALLY SPONSORED RESEARCH

This invention was made with government support under Grant Number AI092033 awarded by the National Institutes of Health. The government has certain rights in the invention.

CLAIM FOR PRIORITY

This application is a U.S. National Stage Application of PCT/US2011/059432 filed on Nov. 4, 2011, which claims priority to U.S. provisional patent application 61/410,112 filed on Nov. 4, 2010, the contents of both of which are incorporated herein by reference.

FIELD

The present invention generally relates at least to the fields of microbiology, molecular biology, infectious disease and medicine. In particular, the invention relates to defensin-like molecules and derivatives and analogs thereof for treating and/or preventing infections in mammals caused by microorganisms, such as bacteria.

BACKGROUND

The ever increasing emergence of many relevant pathogenic strains of bacteria resistant to commonly used antibiotics is a rapidly growing concern in public health. Patients with weakened immunity because of chemotherapy, AIDS or organ transplantation or patients undergoing acute care in hospitals are significantly at risk for acquiring opportunistic bacterial infections. Seven leading groups of pathogens account for the increased risk for such infections, including Gram-positive bacteria: *Staphylococcus aureus, Enterococcus faecium*, streptococci, and coagulase-negative staphylococci. Resistance against commonly used classical antibiotics has emerged in all of these pathogens. Given the increasing rate at which infectious organisms develop resistance to antibiotics currently in use, there is an urgent need to develop novel classes of potent antibiotics against molecular targets, such as lipid II. Lipid II is an ideal target for antibiotics since it is an essential component in bacterial cell wall synthesis. Strategies to find novel antimicrobial (antibacterial) compounds using bacterial genomics approaches have as yet proven largely unsuccessful.

SUMMARY

According to non-limiting example embodiments, the present invention relates to methods of treating and/or preventing infections in mammals caused by microorganisms, such as gram-positive bacteria, by administering to the mammal, a therapeutically effective amount for treating and/or preventing such infections, of one or more defensin-like molecules. The defensin-like molecules bind to lipid II in bacterial membranes and cause death of a bacterial population. Examples of such bacteria may include for example, one or more of *Staphylococcus aureus, Streptococcus pyogenes, Streptococcus agalactiae, Streptococcus anginosus* group, and *Enterococcus faecalis*.

Example embodiments also relate to compositions that include one or more of such molecules. Further examples relate to kits that include one or more of the present defensin-like molecules or compositions including the same, and instructions for their use in treating and/or preventing infections in mammals.

Further embodiments are directed to use of the presently disclosed defensin-like molecules for the prevention or treatment of one or more infections, such as bacterial infections.

In example embodiments, the methods, uses, compositions, and kits of the present invention may include one or more of the following five defensin-like molecules: 5107930, 5100015, 1499-1221, 7771-0701, and 0251-0215.

In other embodiments, the present invention relates to methods for killing a bacterial population or for preventing a bacterial infection comprising administering to a mammalian host infected with said bacterial population a therapeutically effective amount of at least one defensin-like molecule disclosed herein or a composition containing the same.

BRIEF DESCRIPTION OF THE FIGURES

Non-limiting example embodiments are described herein, with reference to the following accompanying Figures.

DETAILED DESCRIPTION

Figure 1:
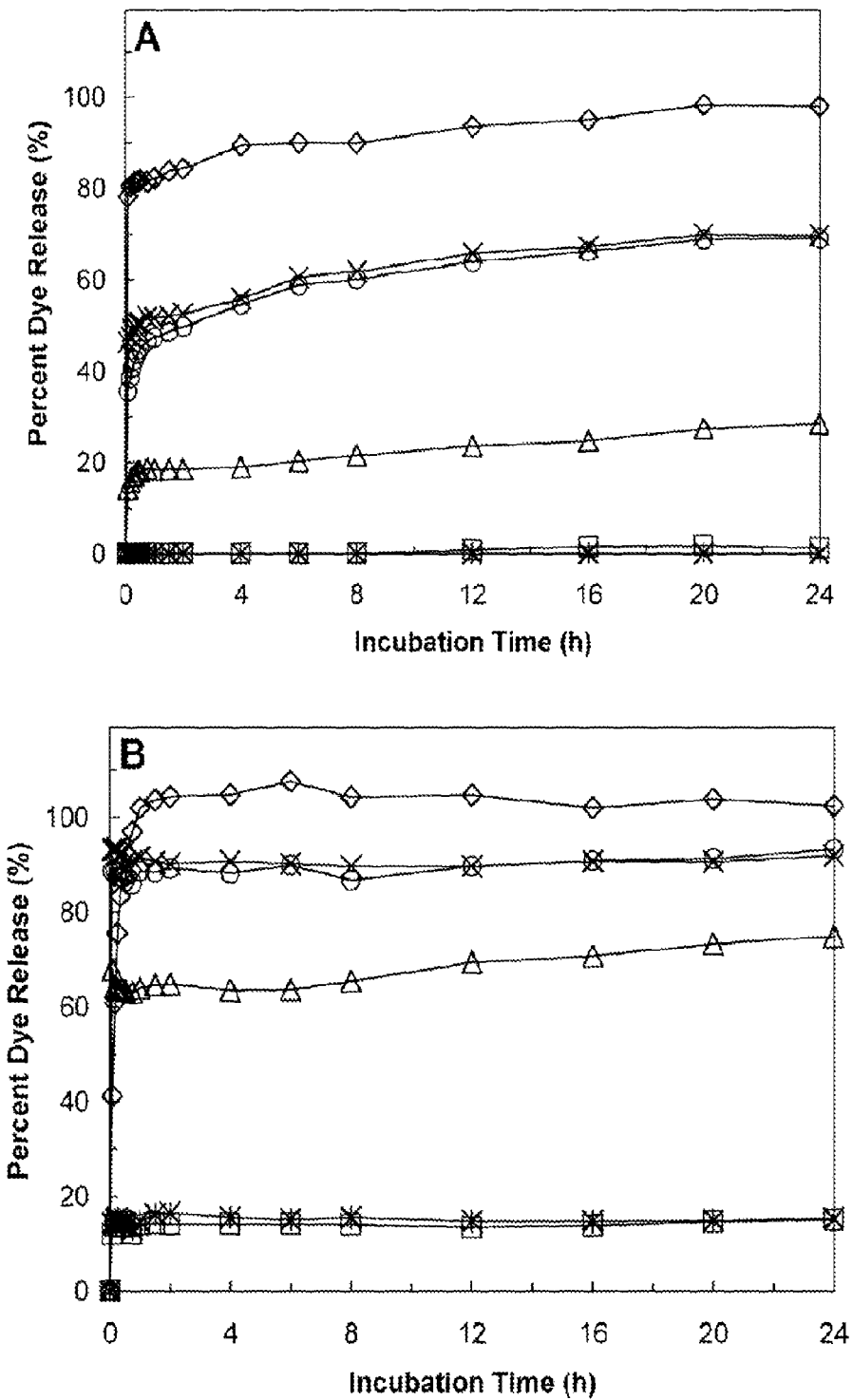
FIG. 1 depicts charts of time-dependent percent release of ANTS-DPX from POPG LUVs induced by the six human α-defensins at 10 µg/ml over a period of 24 h (circle=HNP1, cross=HNP2, triangle=HNP3, diamond=HNP4, star=HD5, square=HD6). (A) At high salt concentration (5 mM HEPES, 100 mM NaCl, pH 7.4); and (B) At low salt concentration (5 mM HEPES, 10 mM NaCl, pH 7.4).

The present inventors have identified Lipid II as a specific target for killing of Gram-positive bacteria by human defensins. Defensins are important (first line) immune defense molecules and despite being structurally conserved, exert diverse effects at the functional level including binding to lipid II molecules in bacterial cell walls. Molecular modeling was used to identify defensin-like molecules that mimic naturally occurring antimicrobial products such as antimicrobial defensin peptides as a step toward development of next-generation therapeutic agents for the treatment of bacterial infections, in particular Gram positive bacterial infections.

The present inventors have identified defensin-like molecules that may be used e.g., to treat or prevent infections in mammals. The present invention provides methods of treating and/or preventing infections in mammals, such as humans, which methods include administering to the mammal a therapeutically effective amount of at least one defensin-like molecule, or derivative or analog thereof, or administering a composition that includes such molecule(s). Example embodiments include administering one or more of the defensin-like molecules disclosed herein. Those skilled in the art would be able to ascertain, which mammals may be treated by the various methods. For example, the mammal may be human or may be other mammals. Thus, methods of treatment may include for example, veterinary applications.

Also provided herein are methods of killing a bacterial population in a mammal that includes administering to a mammal, a therapeutically effective amount for killing a bacterial population of at least one of the disclosed defensin-like molecules.

Also provided are kits that may include one or more of the disclosed compositions or components thereof, and instructions for administering said molecules or compositions to a mammal for prevention or treatment of a bacterial infection. Kits provided herein may additionally include one or more additional components or excipients that may be used to form a composition for administration of the molecule to a mammal, or one or more tools or components that may be used to administer the composition to a mammal.

Additional aspects, advantages and/or other features of example embodiments of the invention will become apparent in view of the following detailed description, taken in conjunction with the accompanying drawings. It should be apparent to those skilled in the art that the described embodiments provided herein are merely exemplary and illustrative and not limiting. Numerous embodiments of modifications thereof are contemplated as falling within the scope of this disclosure and equivalents thereto.

All publications mentioned in this specification are indicative of the level of those skilled in the art to which the invention pertains. All patents and publications herein are incorporated by reference to the same extent as if each individual publication was specifically and individually indicated as having been incorporated by reference in its entirety.

In describing example embodiments, specific terminology is employed for the sake of clarity. However, the embodiments are not intended to be limited to this specific terminology. Unless otherwise noted, technical terms are used according to conventional usage.

As used herein, "a" or "an" may mean one or more. As used herein "another" may mean at least a second or more. Furthermore, unless otherwise required by context, singular terms include pluralities and plural terms include the singular.

Defensins form a large subfamily of cationic antimicrobial peptides that kill a broad range of microorganisms Human defensins are cysteine-rich, cationic peptides with molecular masses ranging from 3 to 5 kDa. Based on the connectivity of the six conserved cysteine residues and sequence homology, human defensins are classified into α and β families. Both families of defensins have similar three-dimensional structures as determined by X-ray crystallography and NMR studies sharing a common fold of three-stranded anti-parallel β-sheets constrained by three intra-molecular disulfide bonds.

Human defensins were discovered originally as natural peptide antibiotics in neutrophils. These defensins were named Human Neutrophil Peptides (HNP) 1-3 of the α-defensin family. Subsequently, a fourth α-defensin was discovered in neutrophils, termed HNP-4

More recently, two additional α-defensins were described, termed Human Defensin 5 and 6 (Jones, D. E., et al., 1992, "Paneth cells of the human small intestine express an antimicrobial peptide gene," *J Biol Chem* 267:23216-23225; Jones, D. E., and C. L. Bevins, 1993, "Defensin-6 mRNA in human Paneth cells: implications for antimicrobial peptides in host defense of the human bowel," *FEBS Lett* 315:187-192.).

Defensins kill bacteria through pore formation in the microbial membrane, causing leakage of intracellular contents and cell lysis. (Kagan, B. L., et al., 1990, "Antimicrobial defensin peptides form voltage-dependent ion-permeable channels in planar lipid bilayer membranes," *Proc Natl Acad Sci USA* 87:210-214; Lehrer, R. I., et al., 1989, "Interaction of human defensins with *Escherichia coli*. Mechanism of bactericidal activity," *J Clin Invest* 84:553-561.)

The specific disruption of the bacterial membrane by defensins is believed to be driven by electrostatic attractions between these cationic peptides and the negatively charged membrane. However, alternative mechanisms for bacterial killing have been proposed, including membrane-independent mechanisms and targeting of intra-cellular compounds by defensins. (Brogden, K. A, 2005, "Antimicrobial peptides: pore formers or metabolic inhibitors in bacteria?" *Nat Rev Microbiol* 3:238-250; Hancock, R. E., et al., 2002, "Role of membranes in the activities of antimicrobial cationic peptides," *FEMS Microbiol Lett* 206:143-149; Wu, M., et al., 1999, "Mechanism of interaction of different classes of cationic antimicrobial peptides with planar bilayers and with the cytoplasmic membrane of *Escherichia coli*," *Biochemistry* 38:7235-7242.)

Recent observations on the bacterial killing by human defensins could not fully be explained by the membrane-disruption model. First, α-Defensins were shown to preferentially kill Gram-positive bacteria, whereas β-defensins kill Gram-negative strains more effectively (Ericksen, B., et al., 2005, "Antibacterial activity and specificity of the six human {alpha}-defensins," *Antimicrob Agents Chemother* 49:269-

275; Zou, G., E. et al., 2007, "Toward understanding the cationicity of defensins: ARG and LYS versus their noncoded analogs," *J Biol Chem*.). However, human β-defensins carry more positive charges, indicating that cationicity of defensins alone does not explain this strain-specificity.

Second, disruption of the membrane via stable pore formation is believed to require peptide structure. However, the present inventors and others have shown that bacterial killing by defensins can be structure independent (de Leeuw, E., et al., 2007, "Structure-dependent functional properties of human defensin," 5. *FEBS Lett* 581:515-520; Maemoto, A., et al., 2004, "Functional analysis of the alpha-defensin disulfide array in mouse cryptdin-4," *J Biol Chem* 279:44188-44196.)

Third, the present inventors recently observed that α-defensins composed entirely of D-amino acids show greatly reduced anti-bacterial activity against *Staphylococcus aureus* compared to the L-peptide, suggesting that the microbial membrane is not the sole target (Wei, G., et al., 2009, "Through the looking glass, mechanistic insights from enantiomeric human defensins". *J Biol Chem* 284:29180-29192.)

As discussed further below, the present inventors have discovered the interaction between the α-defensin Human Neutrophil Peptide 1 (HNP-1) and lipid II levels in the bacterial membrane and have further discovered particular defensin-like molecules or compounds, which may mimic human defensin and have a similar effect with respect to treating or killing bacterial populations and/or preventing their formation in a mammal.

As indicated above, the present inventors having identified defensin-like molecules that may be used e.g., to treat or prevent infections in mammals. Such molecules may be delivered or administered to a mammal for example, in a composition that includes one or more of such molecules, e.g., in a therapeutically effective amount for treating or preventing infections in a mammal. An effective amount or therapeutically effective amount may be determined by one skilled in the art such as a physician or veterinarian, depending e.g., on the type of mammal, its weight or size, and/or age of the mammal, infection being treated or prevented, etc.

Non-limiting example defensin-like molecules that may be used in the present embodiments may include for example, the following Compounds 1-5 or derivatives and analogues thereof:

Compound 1, 5107930

2-[3-(5,5-dimethyl-3-{2-[methyl(phenyl)amino]vinyl}-2-cyclohexen-1-ylidene)-1-propen-1-yl]-3-ethyl-1,3-benzothiazol-3-ium iodide

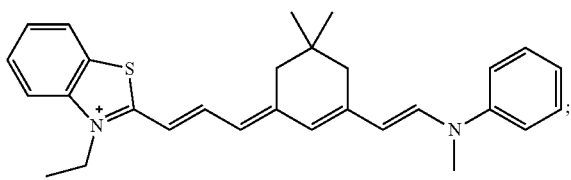

(5107930)

Compound 2, 5100015 pentacyclo[6.6.6.0~2,7~.0~9,14~.0~15,20~]icosa-2,4,6,9,11,13,15,17,19-nonaen-4-ylmethanol

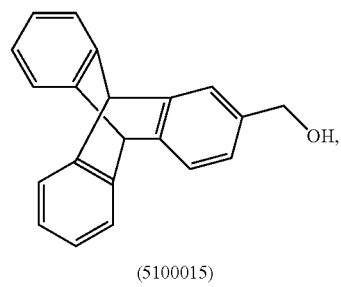

(5100015)

Compound 3, 1499-1221

2-[(E)-2-[4-(dimethylamino)phenyl]ethenyl]-4,6-diphenyl-pyran-3-ylium

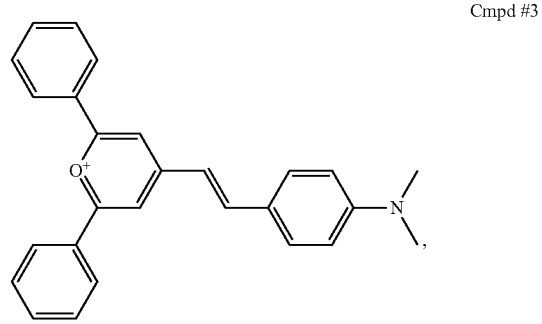

(1499-1221)

Compound 4, 7771-0701

3-ethyl-5-methyl-4-phenyl-2-[3-(1,3,3-trimethyl-1,3-dihydro-2H-indol-2-ylidene)prop-1-en-1-yl]-1,3-thiazol-3-ium

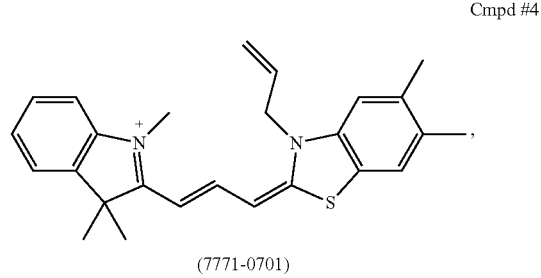

(7771-0701)

and

Compound 5, 0251-0215

4-[(4-fluorophenyl)(4-hydroxyphenyl)methyl]phenol

Cmpd #5

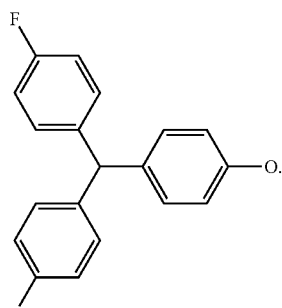

(0251-0215)

Also provided herein are compositions, e.g. for treating or preventing inventions, which include on or more of the above Compounds 1-5, i.e., compounds 5107930, 5100015, 1499-1221, 7771-0701, and 0251-0215.

Further example defensin-like molecules or derivatives or analogs of defensin-like molecules, may include molecules that may be determined based on the present disclosure, which are capable of binding to lipid II in bacterial membranes and cause death of a bacterial population.

Any of the compositions herein may also include one or more pharmaceutically acceptable excipients. Suitable excipients for various types of compositions are well known to those skilled in the art, and suitable excipients may be determined for example based on the desired formulation, e.g., whether the composition is formulated for ingestion and if so, in what form (tablet, capsule, etc), or injection or for another form of administration. Example types of excipients may include for example dyes, flavors, binders, emollients, fillers, lubricants, preservatives, and the like. Example formulations may include e.g., formulations for oral administration or I.V. formulations.

Example embodiments include methods of treating and/or preventing infections in mammals, such as humans, caused by microorganisms. Example methods may include administering to the mammal at least one defensin-like molecule, derivative and/or analog thereof as disclosed herein. Further example methods may include administering to a mammal a therapeutically effective amount of at least one of the defensin-like molecules (e.g., compounds 1-5) disclosed herein.

The defensin-like molecules, may be administered to the mammal (either directly or in a composition) in for example a therapeutically effective amount for treating and/or preventing an infection, such as a bacterial infection. The microorganism may be for example, gram positive bacteria. In particular, the bacteria may include one or more bacteria selected from the group consisting of *Staphylococcus aureus*, *Streptococcus pyogenes*, *Streptococcus agalactiae*, *Streptococcus anginosus* group, and *Enterococcus faecalis*.

Example embodiments are directed to the use of a therapeutically effective amount of one or more of the disclosed defensin-like molecules or derivatives or analogs of defensin-like molecules, or compositions that include such defensin-like molecules or derivatives or analogs thereof, for the treatment of or prevention of an infection of microorganisms in a mammal, such as a human. The molecules, compositions, infections, microorganisms, and mammals are as discussed herein with respect to other embodiments. For example, example embodiments are directed to the use of a therapeutically effective amount of one or more of the following molecules for the treatment of or prevention of an infection of microorganisms in a mammal:

2-[3-(5,5-dimethyl-3-{2-[methyl(phenyl)amino]vinyl}-2-cyclohexen-1-ylidene)-1-propen-1-yl]-3-ethyl-1,3-benzothiazol-3-ium iodide

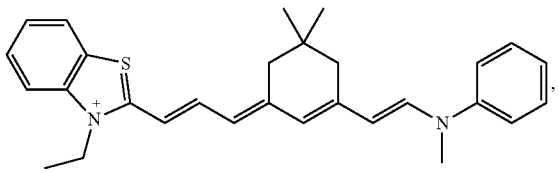

pentacyclo[6.6.6.0~2,7~.0~9,14~.0~15,20~]icosa-2,4,6,9,11,13,15,17,19-nonaen-4-ylmethanol

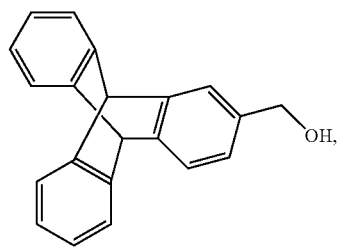 [SMILES: OCc1ccc2c(c1)C1c3ccccc3C2c2ccccc21]

2-[(E)-2-[4-(dimethylamino)phenyl]ethenyl]-4,6-diphenyl-pyran-3-ylium

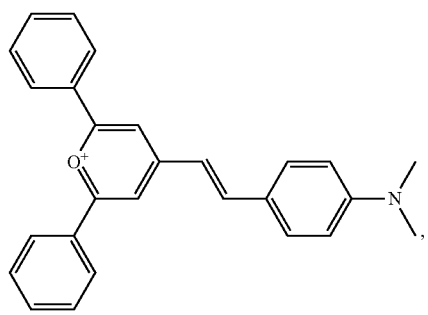

3-ethyl-5-methyl-4-phenyl-2-[3-(1,3,3-trimethyl-1,3-dihydro-2H-indol-2-ylidene)prop-1-en-1-yl]-1,3-thiazol-3-ium

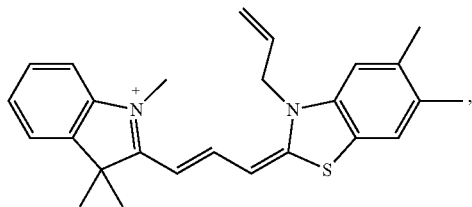

and

4-[(4-fluorophenyl)(4-hydroxyphenyl)methyl]phenol

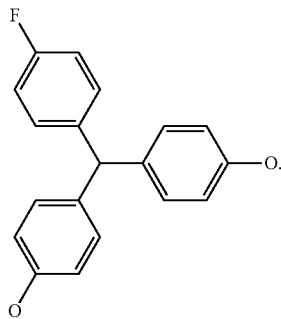

Also provided herein are methods of preventing and/or killing a bacterial population in a mammal. Such methods may include administering to a mammal, a therapeutically effective amount (for killing and/or preventing infection of a bacterial population in the mammal), of at least one defensin-like molecule, for example, in a composition that includes such molecules. The mammal may be for example a mammal that is infected with at least one bacterial population. The present molecules kill the bacterial population in a mammal by binding to lipid II in bacterial membranes and cause death of the bacterial population.

In the case of methods of preventing a bacterial population, the mammal may be for example a mammal who has been exposed to at least one bacteria. The mammal may be for example a mammal having a reduced immunity (e.g., immune compromised) or in a high risk group for severe reaction or complications if infection were to occur (e.g., infant or elderly), who may or may not have been exposed to at least one bacteria. A physician or veterinarian skilled in the art would be able to determine or decide to which particular mammals, the molecules or compositions should be administered.

Example defensin-like molecules, derivatives and/or analogs thereof (i.e, of defensin-like molecules), are as discussed throughout this application. The microorganism may be for example, gram positive bacteria as discussed above. Thus, as indicated above, examples of the bacterial population may include populations of one or more bacteria selected from the group consisting of *Staphylococcus aureus, Streptococcus pyogenes, Streptococcus agalactiae, Streptococcus anginosus* group, and *Enterococcus faecalis*.

Provided herein are example kits that may include at least one molecule selected from the group consisting of defensin-like molecules, derivatives, and analogs thereof or components thereof, or at least one composition that includes one or more molecules selected from the group consisting of defensin-like molecules, derivatives, and analogs thereof; and instructions for administering said molecules or compositions to a mammal for prevention or treatment of a bacterial infection.

A mammal in need of such a composition may include for example, a mammal who has already been infected e.g., with a bacterial population, or it may include mammals at increased risk for becoming infected e.g., with a bacterial population (e.g., by exposure and/or immune-compromised), or mammals who may be at higher risk for becoming infected or for complications or severe reaction in the case of becoming infected. A mammal in need of the composition may be determined by one skilled in the art.

Kits provided herein may additionally include for example, one or more additional components or excipients that may be used in the present compositions, and/or one or more tools or components that may be used to administer the composition to a mammal, such as a syringe, etc.

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXPERIMENTAL EXAMPLES

Example 1

The present examples detail an examination of bacterial killing by α-defensins and demonstrate an interaction with the bacterial target Lipid II.

In this example, the present inventors provide evidence that membrane activity of human α-defensins does not correlate with antibacterial killing. The inventors further show that the α-defensin Human Neutrophil Peptide 1 (HNP-1) binds to the cell wall precursor lipid II and that reduction of lipid II levels in the bacterial membrane significantly reduces bacterial killing. The interaction between defensins and Lipid II suggests the inhibition of cell wall synthesis as a novel antibacterial mechanism of this important class of host defense peptides.

Materials and Methods

Chemicals used for solid phase peptide synthesis were obtained as described in Wu, Z., et al., 2004, "Synthesis and characterization of human alpha-defensins" 4-6 *J Pept Res* 64:118-125. *Staphylococcus aureus* ATCC 29213 was obtained from Microbiologics (St. Cloud, Minn.). The phospholipids palmitoyl-oleoyl-phosphatidylcholine (POPC), palmitoyl-oleoyl-phosphatidylglycerol (POPG) and dipalmitoyl-phosphatidyl choline (DPPC) were purchased from Avanti Polar Lipids (Alabaster, Ala.). 8-aminonaphthalene-1,3,6-trisulfonic acid sodium salt (ANTS) and p-xylenebis (pyridinium) bromide (DPX) were from Molecular Probes (Eugene, Oreg.). Poly-L-lysine (MW=3800) was obtained from Sigma. Bacitracin, D-cycloserine and fosfomycine were purchased from Sigma, Calbiochem and LKT Laboratories respectively.

Solid Phase Peptide Synthesis

Chemical synthesis and folding of defensins was carried out as described in Wu, Z., et al, 2004, "Synthesis and characterization of human alpha-defensins"; Wu, Z., et al., 2003, "Productive folding of human neutrophil alpha-defensins in vitro without the pro-peptide" *J Am Chem Soc* 125:2402-2403. The molecular mass of the peptides was verified by electrospray ionization mass spectrometry (ESI-MS) as described in Wu, Z., et al, 2004, "Synthesis and characterization of human alpha-defensins). Peptide stock solutions prepared with water were quantified spectroscopically using molar extinction coefficients at 280 nm calculated according to the algorithm of Pace et al (Pace, C. N., et al., 1995, "How to measure and predict the molar absorption coefficient of a protein," *Protein Sci* 4:2411-2423.).

LUVs Preparation

Large unilamellar vesicles (LUVs) with the low molecular weight fluorophore/quencher pair (ANTS/DPX) encapsulated were prepared using the standard extrusion method. Specifically, phospholipids were dissolved in chloroform at a desired molar ratio, dried as a film by solvent evaporation. After removal of residual solvent, the lipid film was hydrated in the fluorescent solution containing 5 mM HEPES, 12.5 mM ANTS, 45 mM DPX, and 20 mM NaCl, pH 7.0, freeze-thawed for 10 cycles and extruded 10 times through 0.4-μm polycarbonate membranes. LUVs were separated from unencapsulated materials by gel filtration chromatography using a Sepharose CL-4B column eluted with 5 mM HEPES, 100 mM NaCl, pH 7.4 (high-salt). For leakage assays in a low-salt buffer, purified vesicles were further diluted with 5 mM HEPES containing 10 mM NaCl, pH 7.4.

Leakage Assay

Leakage of ANTS from LUVs, monitored on a LS-55 Perkin Elmer luminescence spectrometer, was characterized by an increase in fluorescence, which was quenched by DPX when encapsulated together inside liposomes (Ellens, H., et al., 1985, "H+- and Ca2+-induced fusion and destabilization of liposomes," *Biochemistry* 24:3099-3106). 270 μl ANTS/DPX-encapsulated LUVs (in either high-salt or low-salt buffers) were added to each well of a 96-well plate to a final lipid concentration of 600 μM. 30 μl $H_2O$ was added to the first well of each row as a blank, and 30 μl 2.5% (v/v) Triton X-100 to the last (twelfth) well as the control for 100% leakage. Upon addition of 30 μl of a twofold dilution series of defensin, the fluorescence signal was recorded at 515 nm with an excitation wavelength of 353 nm, 10 nm bandwidths and a 390 nm cut-off filter in the emission path. Percent leakage is expressed as:

$$\% \text{ leakage} = ((F_t - F_0)/(F_{100} - F_0)) \times 100$$

where $F_t$ is the fluorescence determined at different time points after addition of defensin, $F_0$ is the background fluorescence of the "blank" cells, and $F_{100}$ is the fluorescence of the control cells containing 0.25% Triton X-100.

Lipid II Purification

Short-chain water-soluble Lipid II containing a lipid tail of three isoprene units was generated and purified essentially as described in Breukink, E., et al., 2003, "Lipid II is an intrinsic component of the pore induced by nisin in bacterial membranes," *J Biol Chem* 278:19898-19903.

Typically, *M. flavus* vesicles (120 μmol lipid-Pi) were incubated together with 500 μmol UDP-GlcNAc, 500 μmol UDP-MurNAC-pentapeptide and 400 μmol farnesyl phosphate in 100 mM Tris-HCl pH 8.0, 5 mM $MgCl_2$. The incubation lasted two hours at room temperature for 3-P. The synthesis of 3-Lipid II was followed using RP-8 reversed phase TLC (Merck) developed in 75% methanol. For purification, the membranes were removed by centrifugation at 40,000×g and the supernatant was collected and loaded on a C18 HPLC column and eluted with a linear gradient from 50 mM ammonium bicarbonate to 100% methanol in 30 minutes. Farnesyl-Lipid II (3-Lipid II) eluted at approximately 60% methanol. Its identity was confirmed by mass spectroscopy.

Surface Plasmon Resonance

Surface Plasmon Resonance binding experiments were carried out on a BIAcore T100 system (BIAcore Inc., Piscataway, N.Y.) at 25° C. The assay buffer was 10 mM HEPES, 150 mM NaCl, 0.05% surfactant P20, pH 7.4 (±3 mM EDTA). L-HNP1 (780 RUs) or D-HNP1 (790 RUs) were immobilized on CM5 sensor chips using the amine-coupling chemistry recommended by the manufacturer. Lipid II was introduced into the flow-cells at 30 μl/min in the running buffer. Association and dissociation were assessed for 300 and 600 second, respectively. Resonance signals were corrected for nonspecific binding by subtracting the background of the control flow-cell. After each analysis, the sensor chip surfaces were regenerated with 15 mM HCl for 30 s at a flow rate 100 μl/min, and equilibrated with the buffer prior to next injection. Binding isotherms were analyzed with manufacturer-supplied software for BIAcore T100 and/or GraphPad Prism 4.0.

Antibacterial Activity Assay

The antibacterial activity of HNP1 against *Staphylococcus aureus* ATCC 29213 was carried out in a 96-well turbidimetric assay essentially as described in Ericksen, B., et al., 2005, "Antibacterial activity and specificity of the six human {alpha}-defensins." Lipid II levels in *S. aureus* were manipulated by the addition of three different inhibitors of cell wall synthesis: bacitracin (250 μg/ml), D-cycloserine (64 μg/ml) and fosfomycine (250 μg/ml). Bacterial cultures were pre-treated with these compounds for 30 min under shaking at 37° C. Subsequently, cells were exposed to HNP1 peptide ranging from 256 to 1 μg/ml for 15 min, after which HNP1 activity was neutralized by the addition of Mueller Hinton broth. Bacterial growth was monitored for 12 hours and data were analyzed as described.

Results—Membrane Lipid Interaction of α-Defensins

Defensins are believed to kill bacteria by permeabilizing the membrane, causing leakage of intracellular content and eventually cell lysis and death. The present inventors tested the ability of six human α-defensins to induce leakage of fluorophores encapsulated in LUVs (See FIG. 1). FIG. 1 shows time-dependent leakage curves for HNP1-4 and HD5-6 with phosphatidylglycerol (POPG) LUVs at high and low salt concentrations over a period of 24 h. In particular, FIG. 1 shows time-dependent percent release of ANTS-DPX from POPG LUVs induced by the six human α-defensins at 10 μg/ml over a period of 24 h (circle=HNP1, cross=HNP2, triangle=HNP3, diamond=HNP4, star=HD5, square=HD6). (A) At high salt concentration (5 mM HEPES, 100 mM NaCl, pH 7.4). (B) At low salt concentration (5 mM HEPES, 10 mM NaCl, pH 7.4). LUVs were 250 nm in diameter and 600 μM (phospholipids) in concentration.

All the six α-defensins tested at concentrations ranging from 0.19 to 100 μg/ml, whenever capable of inducing liposomal leakage, were fast acting as evidenced by a fluorescence plateau reached within the first hour. The plateau effect reflects the observation that at the start of the experiment the fractional fluorescence increases rapidly due to leakage of ANTS and DPV from the vesicles into the exterior solution, after which dilution removes the quenching effect of DPX. The observed differences between individual defensins over time likely reflect differences in the kinetics of induction of LUV leakage. Membrane activity of defensins invariably decreased at high salt concentrations and varied significantly between the defensins tested.

Next, the present inventors examined the effects of negative surface charge on defensin-induced membrane leakage.

HNP1 was used extensively in the laboratory as a model for α-defensins in these experiments. (Zou, G., et al., 2007. "Toward understanding the cationicity of defensins: ARG and LYS versus their noncoded analogs," *J Biol Chem*; Wei, G., E. et al., 2009, "Through the looking glass, mechanistic insights from enantiomeric human defensins," *J Biol Chem* 284: 29180-29192; Wu, Z., et al., 2007, "Impact of pro segments on the folding and function of human neutrophil alpha-defensins," *J Mol Biol* 368:537-549; Zou, G., E. de Leeuw, J. Lubkowski, and W. Lu, 2008, "Molecular determinants for the interaction of human neutrophil alpha defensin 1 with its propeptide," *J Mol Biol* 381:1281-1291).

To elucidate the role of electrostatic forces in defensin-induced membrane leakage, the inventors prepared LUVs composed of the unsaturated lipid pair POPC (charge: 0) and POPG (charge: −1) at four different ratios, i.e., POPC: POPG=1:0, 3:2, 2:3, and 0:1. As shown in FIG. 2A, leakage from LUVs became increasingly pronounced across the entire HNP1 concentration range as the content of the negatively charged lipid POPG increased from 0, 40%, 60% to 100%, equivalent to a charge on the membrane surface of 0, −0.4, −0.6 and −1, respectively. LUVs composed solely of the neutral lipid POPC were resistant to the attack by HNP1 at all concentrations used, regardless of the incubation time. The inventors recently reported that HNP1 composed entirely of D-amino acids (D-HNP1) was significantly less bactericidal than L-HNP1 against *S. aureus* (Wei, G., E. et al., 2009, "Through the looking glass, mechanistic insights from enantiomeric human defensins"). The inventors compared the ability of both L- and D-HNP1 to induce leakage from LUVs (DPPC/POPG (1:1)) and no significant difference in activity between the two enantiomers was found. (See FIG. 2B).

Figure 2:
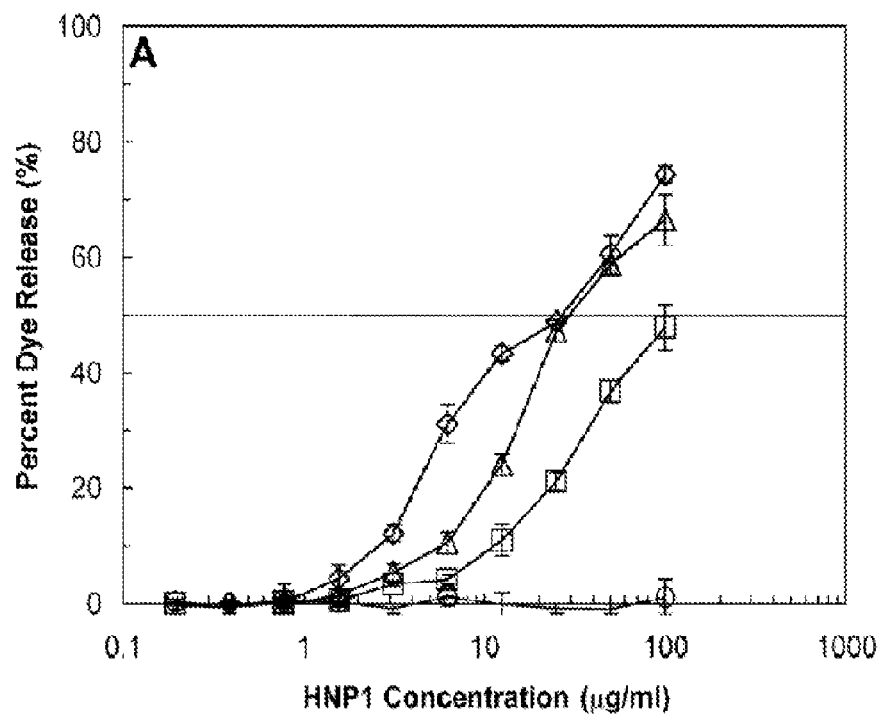
FIG. 2. depicts charts showing (A) effects of surface charge on HNP1-induced leakage from LUVs of four different compositions: POPC (circle, surface charge=0), POPC/POPG=3:2 (square, surface charge=−0.4), POPC/POPG=2:3 (triangle, surface charge=−0.6), and POPG (diamond, surface charge=−1). (B) LUV (POPG:DPPC 1:1) leakage induced by L-HNP1 (circles) or D-HNP1 (squares).
Figure 2:
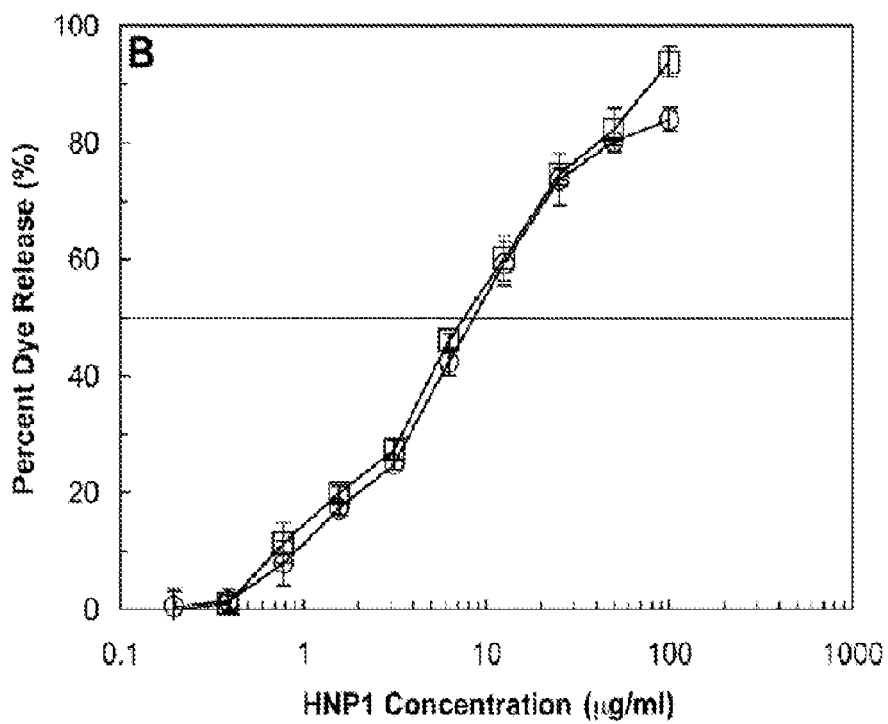

In particular, FIG. 2 shows the following. (A) Effects of surface charge on HNP1-induced leakage from LUVs of four different compositions: POPC (circle, surface charge=0), POPC/POPG=3:2 (square, surface charge=−0.4), POPC/POPG=2:3 (triangle, surface charge=−0.6), and POPG (diamond, surface charge=−1). (B) LUV (POPG:DPPC 1:1) leakage induced by L-HNP1 (circles) or D-HNP1 (squares). A two-fold dilution series of HNP1 peptides from 0.19 to 100 μg/ml was incubated with 600 μM LUVs for one hour before readings were taken. Error bars indicate the standard error in triplicate experiments.

Taken together, these findings suggest that defensin-induced permeabilization of lipid vesicles depends on electrostatic interaction, however varies greatly between different α-defensins. Most importantly, the ability of individual α-defensins to cause membrane leakage (FIG. 1) correlates poorly with their ability to kill bacteria (Ericksen, B., et al., 2005, "Antibacterial activity and specificity of the six human {alpha}-defensins"). For example, HNP4, the most membrane active defensin in the panel of six (FIG. 1), is ineffective against Gram-positive bacteria Id. Vice versa, HNP1 and HD-5 are potently bactericidal, however display reduced, or in the case of HD-5 little membrane activity even at high concentrations. Finally, our observation that D-HNP1 and L-HNP1 disrupt LUVs equally efficiently suggests that native HNP1 preferentially interacts with a bacterial membrane component, possibly of chiral nature.

HNP1 Binds to Lipid II

Recently, α-defensins were shown to bind with high affinity to glycosylated proteins (Wang, W., et al., 2004, "Activity of alpha- and theta-defensins against primary isolates of HIV-1," *J Immunol* 173:515-520) and carbohydrates (Lehrer, R. I., G. Jung, P. Ruchala, S. et al., 2009, "Multivalent binding of carbohydrates by the human alpha-defensin," HD5. *J Immunol* 183:480-490). HNP1 kills Gram-positive bacteria very efficiently, however showed reduced membrane leakage, especially at high salt concentrations. The present inventors theorized that defensins could interact with components of the bacterial cell wall or cytoplasmic membrane. The inventors studied the possibility of an interaction between defensins and Lipid II, a peptidoglycan precursor. D-HNP1 and a linear form of HNP1 were studied also because both linear as well as enantiomeric α-defensin peptides appeared less bactericidal against *S. aureus*, but equally bactericidal against *E. coli* (de Leeuw, E., et al., 2007, "Structure-dependent functional properties of human defensin", Wei, G., E, et al., 2009, "Through the looking glass, mechanistic insights from enantiomeric human defensins").

Figure 3:
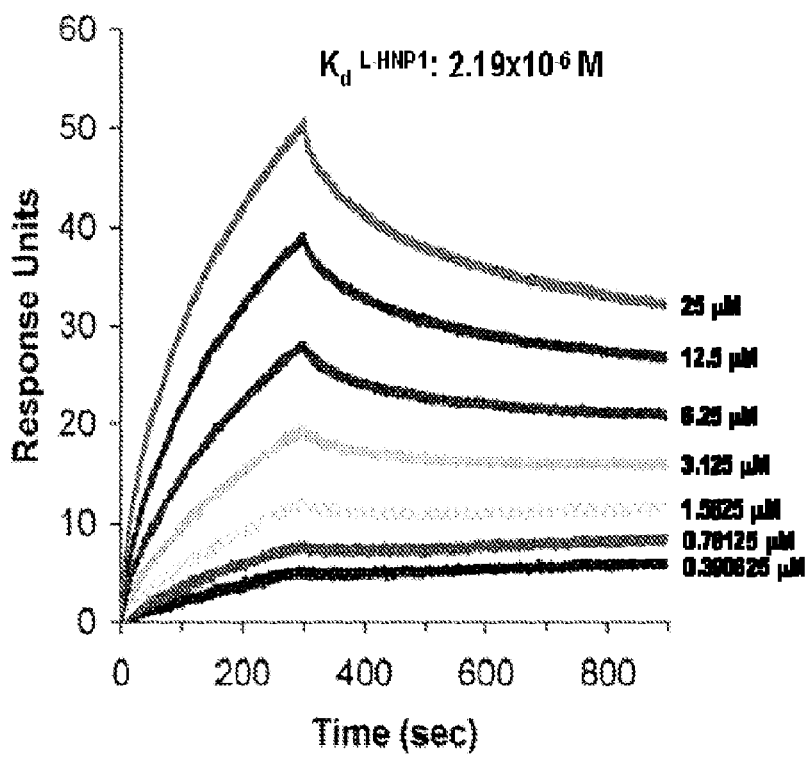
FIG. 3 depicts binding kinetics of soluble Lipid II on immobilized HNP1 as determined by SPR at room temperature. Representative sensorgrams of one out of two separate experiments of soluble Lipid II (from 20 to 0.390625 µM) using a sensorchip with 780 RUs of L-HNP1 (left panel) or 790 RUs of D-HNP1 (right panel).
Figure 3:
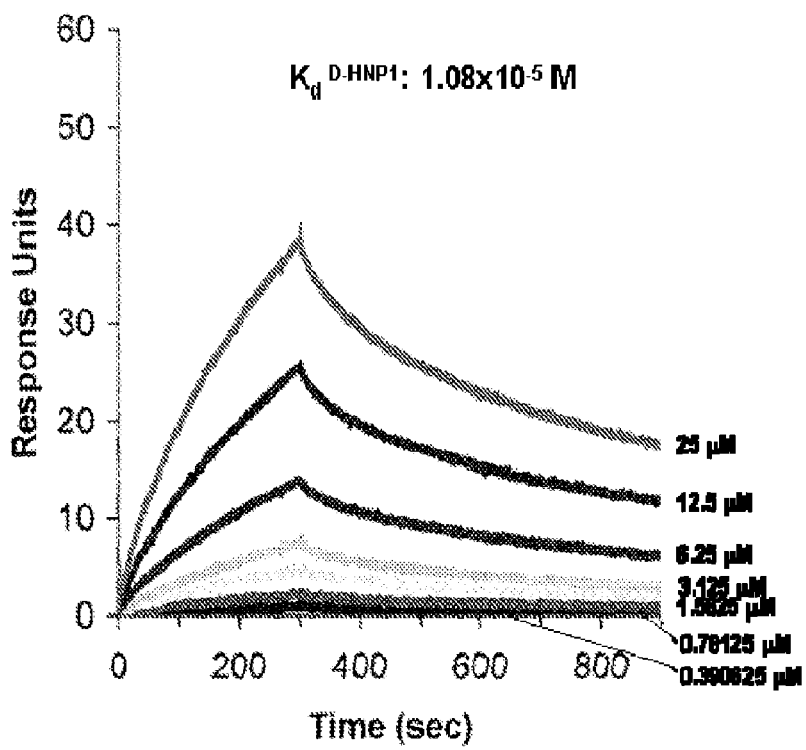

The inventors used a Surface Plasmon Resonance (SPR) approach to determine the binding of HNP1 to Lipid II directly. Initial binding of L-HNP1, D-HNP1 and linear HNP1 to soluble Lipid II immobilized on the chip surface was determined. Linear HNP1 showed little or no binding to Lipid II at 0.1, 1 or at 10 μM. Both L- and D-HNP1 bound Lipid II dose-dependently, however binding of wild-type HNP-1 was more efficient than that of the D-form. Conversely, the L- and D-HNP1 peptides were individually immobilized on a CM5 chip and binding of the purified, soluble form of Lipid II ranging in concentration from 25 to 0.78 μM to both peptides was determined. As shown in FIG. 3, soluble Lipid II bound to both the L-form as well as the D-form of HNP1. In particular, FIG. 3 demonstrates binding kinetics of soluble Lipid II on immobilized HNP1 as determined by SPR at room temperature. Representative sensorgrams of one out of two separate experiments of soluble Lipid II (from 20 to 0.390625 μM) using a sensorchip with 780 RUs of L-HNP1 (left panel) or 790 RUs of D-HNP1 (right panel). Indicated $K_d$ values represent the average of the two separate experiments (individual values: L-HNP-1: $1.79 \times 10^{-6}$ and $2.59 \times 10^{-6}$; D-HNP-1: $1.11 \times 10^{-5}$ and $1.05 \times 10^{-5}$ respectively).

Fitting of the kinetic data to a 1:1 binding model indicated that Lipid II binds the L-HNP1 peptide with an approximately five times higher affinity than the D-peptide ($2.19 \times 10^{-6}$ M vs. $1.08 \times 10^{-5}$ M).

HNP1 Functionally Interacts with Lipid II

To examine whether the observed interaction between HNP1 and Lipid II is functionally relevant in the environment of the membrane, the inventors determined the ability of HNP1 to kill *S. aureus* with altered levels of Lipid II. Three different inhibitors of cell wall synthesis, fosfomycine, D-cycloserine, and bacitracin, were used to reduce the lipid II levels in *S. aureus* cells. Bacitracin binds directly to undecaprenyl pyrophosphate, the portion of lipid II that remains in the membrane once GlcNAc-MurNAc is polymerized, and prevents its use in subsequent cycles of lipid II synthesis. Fosfomycine is an inhibitor of MurA, the enzyme responsible for the first step in peptidoglycan synthesis. D-Cycloserine inhibits both alanine racemase and D-Ala-D-Ala ligase, two enzymes required for the synthesis of the D-Ala-D-Ala dipeptide of lipid II. All three inhibitors thus block the synthesis of lipid II (Lunde, C. S., et al., 2009, "Telavancin disrupts the functional integrity of the bacterial membrane through targeted interaction with the cell wall precursor lipid II," *Antimicrob Agents Chemother* 53:3375-3383.) *S. aureus* cells were exposed to each of the Lipid II synthesis inhibitors for 30 min and subsequently exposed to HNP1 at concentrations ranging from 256 to 1 μg/ml for 15 min (FIG. 4).

Figure 4:
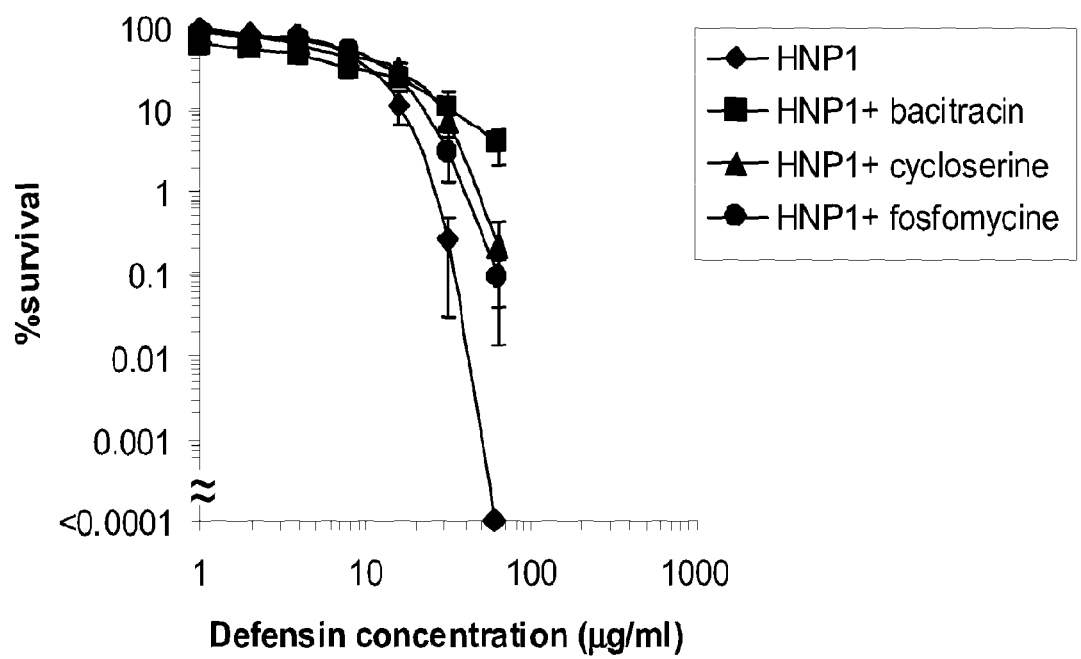
FIG. 4 is a chart depicting Lipid II-dependent bacterial killing by HNP1. Survival curves are shown of *S. aureus* ATCC 29213 exposed to HNP1 at concentrations varying two-fold from 1 to 256 µg/ml. Bacteria were pre-treated with bacitracin (250 µg/ml), D-cycloserine (64 µg/ml) and fosfomycine (250 µg/ml) for 30 min under shaking at 37° C. as indicated, followed by exposure to HNP1 for 15 min.

FIG. 4 demonstrates Lipid II-dependent bacterial killing by HNP1. Survival curves of *S. aureus* ATCC 29213 exposed to HNP1 at concentrations varying two-fold from 1 to 256 μg/ml. Bacteria were pre-treated with bacitracin (250 μg/ml), D-cycloserine (64 μg/ml) and fosfomycine (250 μg/ml) for 30 min under shaking at 37° C. as indicated, followed by exposure to HNP1 for 15 min. Each curve is the mean of three separate experiments (±S.D.). Points scored as zero survival could not be plotted.

Following pre-treatment with Lipid II biosynthesis inhibitors and exposure of HNP-1 to the bacteria for 2 hours, according to the inventors' original protocol (Ericksen, B et al., 2005, "Antibacterial activity and specificity of the six human {alpha}-defensins"), the inventors observed no difference in bacterial killing (data not shown). The inventors believe that most likely, the effects of any bacterial pre-treatments are negated by killing efficiency and kinetics of HNP1 during the prolonged, two hour exposure to the bacteria. As observed previously, after 15 min, HNP1 efficiently killed *S. aureus* (Zou, G., et al., 2007, "Toward understanding the cationicity of defensins. Arg and Lys versus their noncoded analogs," *J Biol Chem* 282:19653-19665.) At peptide concentrations of 256 and 128 μg/ml, bacterial growth did not measurably recover after 12 h incubation and data points could not be plotted. Fosfomycine and D-cycloserine and in particular bacitracin treatment attenuated killing of *S. aureus* by HNP1 markedly. Taken together, these data indicate that efficient killing of *S. aureus* by HNP1 depends on membrane lipid II levels.

Discussion

Disruption of the functional integrity of the bacterial membrane is a common mode of action of many antibacterial compounds and is believed to be the primary mode of bacterial killing by defensins. An early study reported on the bactericidal activity of HNP1-3 against *E. coli*, suggesting a sequential permeabilization of the outer and inner membranes (Lehrer, R. I., et al., 1989, "Interaction of human defensins with *Escherichia coli*. Mechanism of bactericidal activity".) More recent observations on the bactericidal activity of α-defensins have expanded and nuanced these findings. The present inventors and others reported that linear, unstructured defensins retained their antibacterial activity in a strain-selective manner (de Leeuw, E., et al., 2007, "Structure-dependent functional properties of human defensin"; Hadjicharalambous, C., et al., 2008, "Mechanisms of alpha-defensin bactericidal action: comparative membrane disruption by Cryptdin-4 and its disulfide-null analogue," *Biochemistry* 47:12626-12634.) The activity of HD-5 against *E. coli* appeared structure-independent, whereas the unstructured peptide showed greatly reduced activity against *S. aureus* (de Leeuw, E., et al., 2007, "Structure-dependent functional properties of human defensin"). More recently, the inventors observed that the D-forms of HNP1 and HD-5 were significantly less active than their native L-forms against *S. aureus*, but equally bactericidal against *E. coli* (Wei, G., et al., 2009, "Through the looking glass, mechanistic insights from enantiomeric human defensins".) Combined, these findings suggested different bactericidal mechanisms of α-defensins against *E. coli* or *S. aureus*. In addition, these findings suggested a possible interaction between defensins and an unidentified cellular component of *S. aureus*.

The present inventors found that HNP1 functionally interacts with lipid II, an essential precursor of cell wall synthesis. A number of antibacterial compounds target lipid II, thus affecting cell wall synthesis or membrane function Id. For example, the antibacterial action of nisin, an amphiphilic peptide produced by certain strains of *Lactococcus lactis*, is a result of its high affinity for lipid II as well as its ability to assemble into nisin-lipid II complexes (Breukink, E., et al., 2003, "Lipid II is an intrinsic component of the pore induced by nisin in bacterial membranes," *J Biol Chem* 278:19898-19903.) Such complexes have the ability to form pores in the membrane, explaining the high efficacy of nisin (Breukink, E., I. et al, 1999, "Use of the cell wall precursor lipid II by a pore-forming peptide antibiotic," *Science* 286:2361-2364). Here, the inventors show that bacterial killing by α-defensins depends on lipid II levels by blocking the synthesis of lipid II. All three lipid II synthesis inhibitors reduced bacterial killing, in particular when *S. aureus* cells were pretreated with bacitracin. A similar observation was made recently in the case of nisin (Lunde, C. S., et al, 2009, "Telavancin disrupts the functional integrity of the bacterial membrane through targeted interaction with the cell wall precursor lipid II.") In this study, depolarization of the *S. aureus* membrane induced by nisin was suppressed by pretreatment of cells with lipid II inhibitors, especially by bacitracin. Interestingly, nisin and bacitracin share a common target in binding the lipid II molecule, both binding the pyrophosphate moiety of undecaprenyl-pyrophosphate. Because the antibacterial activity of both nisin and defensin was reduced most strongly by treatment with bacitracin, defensins, like nisin, may use lipid II as an initial binding target and perhaps even similarly disrupt the membrane via complex pore formation.

The inventors' observation that HNP1 binds to lipid II partly rationalizes the inventors' previous findings on the strain-selective and structure-dependent difference in bactericidal activity of human α-defensins. However, questions still remained why α-defensins preferentially kill Gram-positive bacteria. For example, the inventors found that D-HNP1 binds to lipid II with a five-fold weaker affinity than the L-form. This difference could be explained by the fact that lipid II itself is a chiral molecule. However, D-HNP1 was found to be ~19 times weaker in *S. aureus* killing compared to L-HNP1 as judged by their respective vLD90 values, defined as the defensin concentration required to kill 90% of bacteria (Wei, G., et al., 2009, "Through the looking glass, mechanistic insights from enantiomeric human defensins.") Defensins therefore may interact with other membrane components in addition to lipid II.

Other possible interactions at the bacterial membrane could include negatively charged molecules such as (lipo) teichoic acid in the case of Gram-positive bacteria or lipopolysaccharide or teichoic acid in the case of Gram-negative bacteria. Precursors of teichoic acid synthesis are, like Lipid II, undecaprenyl-linked (Neuhaus, F. C., et al., 2003, "A continuum of anionic charge: structures and functions of D-alanyl-teichoic acids in gram-positive bacteria," *Microbiol Mol Biol Rev* 67:686-723.), and may therefore constitute a possible binding target for HNP1 also. In addition, the inventors observed that bacterial killing by α-defensins correlates poorly with their lipid membrane activity. Nevertheless, increase of negative charge of the phospholipid headgroup increased HNP1 membrane activity, suggesting that bactericidal activity may involve direct defensin-lipid interactions. In summary, the inventors' findings suggest the inhibition of peptidoglycan synthesis through binding of lipid II as a novel mechanism of bacterial killing for defensins.

Example 2

Figure 5:
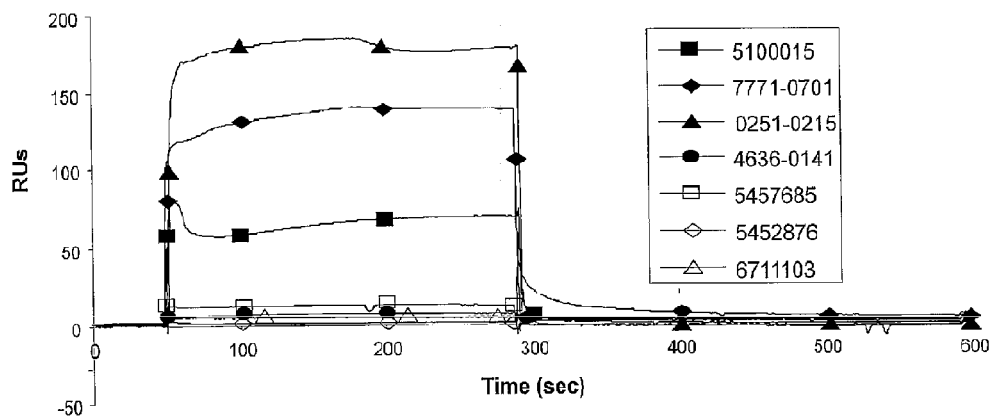
FIG. 5 demonstrates that binding of certain compounds of interest (including some of the molecules that may be used in accordance with the present invention) to 3-Lipid II correlates with anti-bacterial killing.
Figure 5:
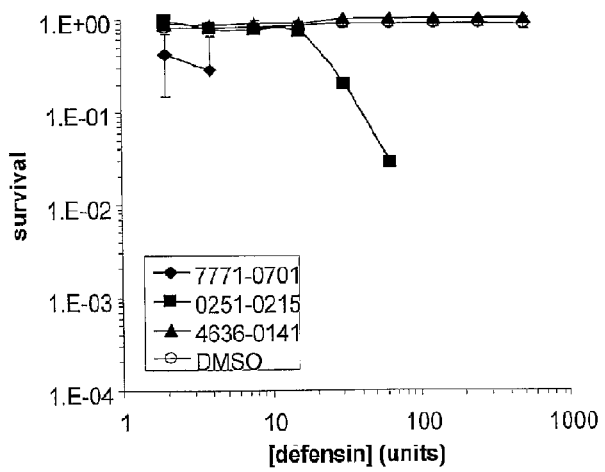
Figure 5:
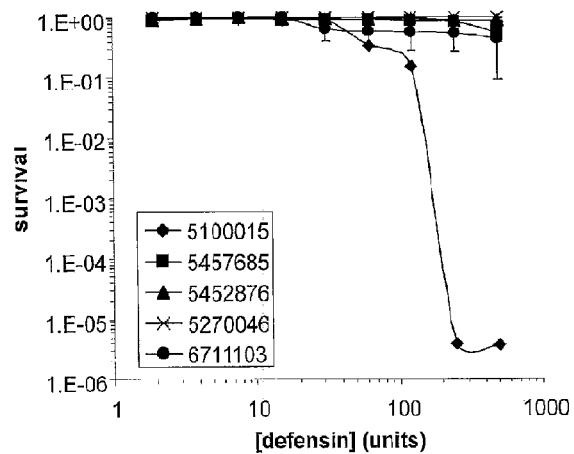

In this example, a similarity search was conducted based on the interaction between HNP-1 and Lipid II identified compounds mimicking this interaction. These compounds were subsequently tested for bacterial killing and cytotoxicity. Based on these assays, compounds of interest as being possible defensin-like compounds were identified based on the following criteria:

1) Specificity for killing of the Gram-positive bacterium *S. aureus* over killing of the Gram-negative bacterium *E. coli*, 2) Acceptable cytotoxicity as measured by cell viability assays The present inventors examined if the identified compounds themselves directly interact with Lipid II, which would be expected if they mimic the binding of HNP-1. Binding of compounds was tested directly using Surface Plasmon Resonance with 3-Lipid II immobilized on the chip surface (FIG. 5). The inventors found that compounds selected on the two criteria listed above bind to Lipid II. In particular, the following compounds were identified 5100015, 7771-0701 and 0251-0251, which compounds are also very efficient in killing of *S. aureus*.

As control, the inventors used compounds that were identified by the similarity search and didn't show any bactericidal activity against *S. aureus*. (4636-0141, 5457685, 5452876, 5270046 and 6711103). None of these compounds showed binding to Lipid II. This suggests that binding to Lipid II by compounds of interest (5100015, 7771-0701 and 0251-0251) are linked to *S. aureus* killing, and these compounds are therefore defensin-like molecules.

Figure 6:
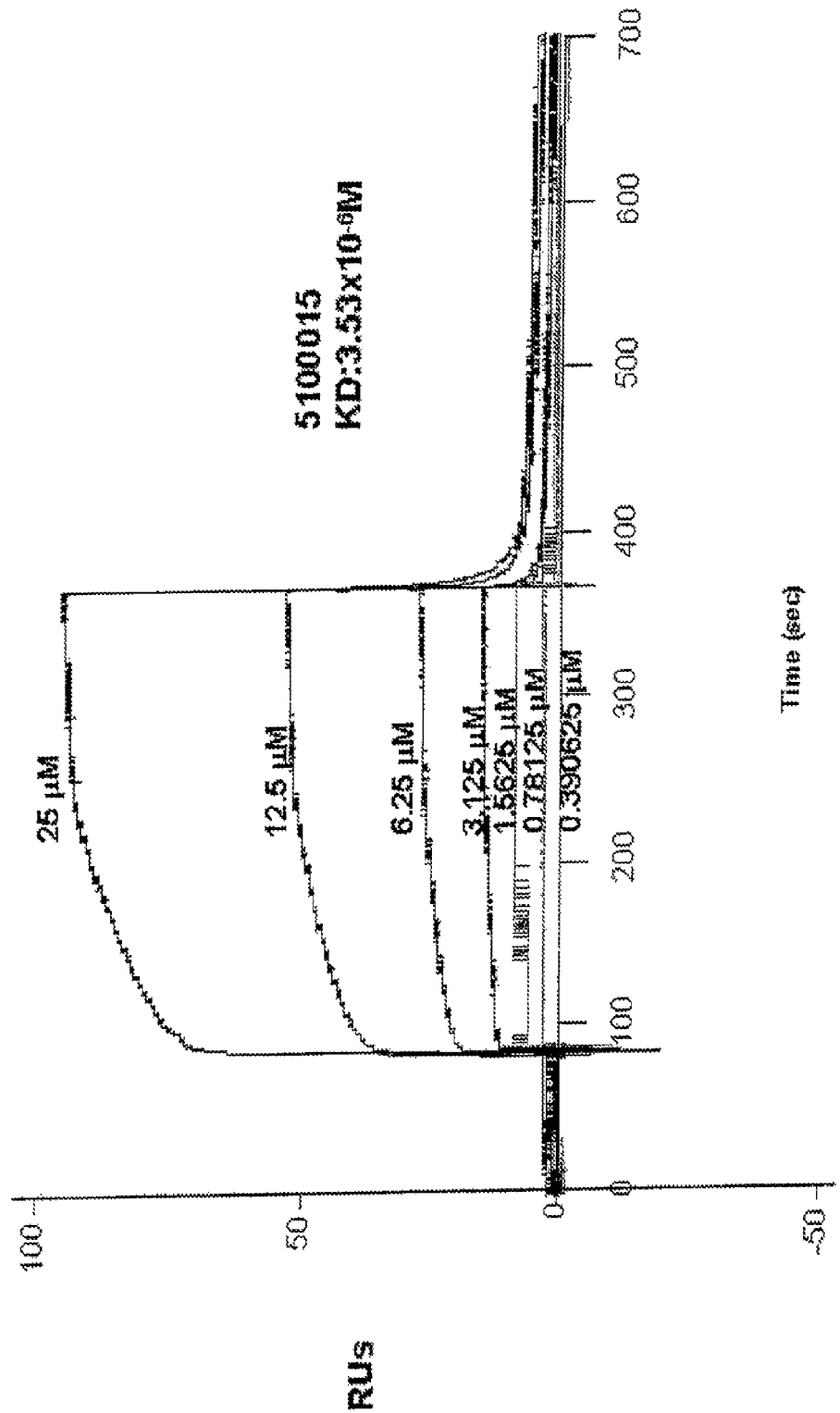
FIG. 6 shows binding affinity curves of Compound 2, 5100015, to immobilized 3-Lipid II.

The present inventors determined the binding affinities for the three compounds, 5100015, 7771-0701 and 0251-0215, using Surface Plasmon Resonance. FIG. 6 shows binding affinity curves of 5100015 as an example.

Example 3

Based on the studies of Example 2, a second round of similarity searches were performed, using compounds of interest from the first search.

The aims of the similarity searches were as follows:

1. Searching for compounds that structurally similar to the active compounds.

2. Searching for compounds that have similar physiochemical properties to the active compounds. Note that these compounds have a lower probability of being active, but could identify novel chemical structures for further analysis.

Methods

1. Chemical similarity searches using MOE BIT-MACCS fingerprint.

2. Physiochemical similarity searches using MOE MPMFP fingerprint.

Query Compounds

Figure 7:
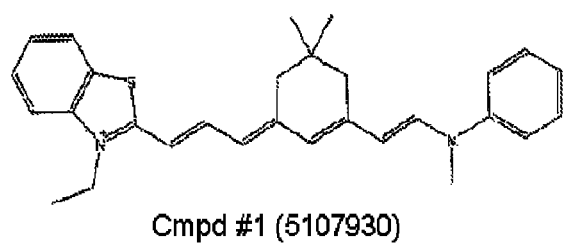
FIG. 7 depicts Compounds 1-5 discussed herein, which may be used in accordance with various embodiments of the present invention.
Figure 7:
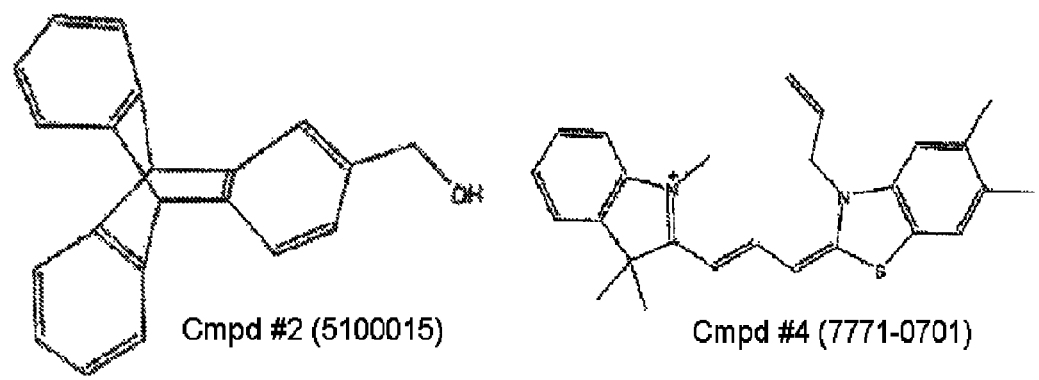
Figure 7:
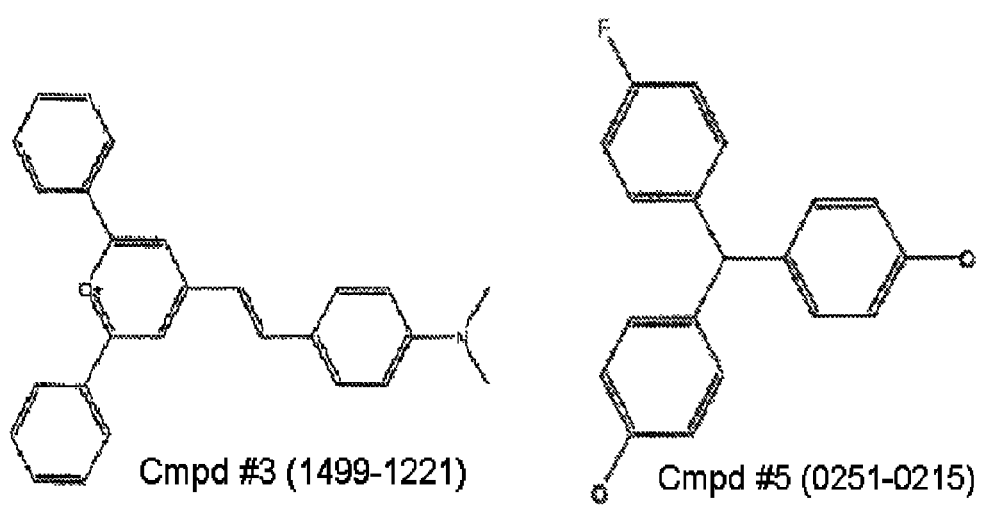

Query compounds 1-5, which were identified as being possible defensin-like molecules that may be used in preventing or treating infections, are depicted in FIG. 7. In particular, Compound 1 is identified as 5107930, Compound 2 is identified as 5100015, Compound 3 is identified as 1499-1221, Compound 4 is identified as 7771-0701, and Compound 5 is identified as 0251-0215. The structures of these compounds are set forth below.

Compound 1, 5107930

2-[3-(5,5-dimethyl-3-{2-[methyl(phenyl)amino]vinyl}-2-cyclohexen-1-ylidene)-1-propen-1-yl]-3-ethyl-1,3-benzothiazol-3-ium iodide

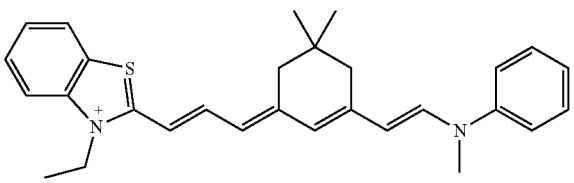

Compound 2, 5100015 pentacyclo[6.6.6.0~2,7~.0~9,14~.0~15,20~]icosa-2,4,6,9,11,13,15,17,19-nonaen-4-ylmethanol

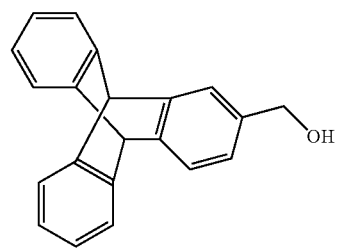 [SMILES: OCc1ccc2c(c1)C1c3ccccc3C2c2ccccc21]

Compound 3, 1499-1221

2-[(E)-2-[4-(dimethylamino)phenyl]ethenyl]-4,6-diphenyl-pyran-3-ylium

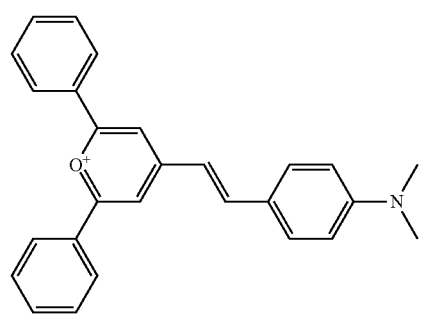 [SMILES: CN(C)c1ccc(/C=C/c2cc(-c3ccccc3)[o+]c(-c3ccccc3)c2)cc1]

Compound 4, 7771-0701

3-ethyl-5-methyl-4-phenyl-2-[3-(1,3,3-trimethyl-1,3-dihydro-2H-indol-2-ylidene)prop-1-en-1-yl]-1,3-thiazol-3-ium

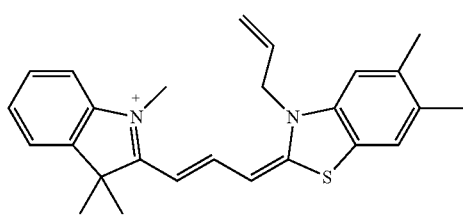

Compound 5, 0251-0215

4-[(4-fluorophenyl)(4-hydroxyphenyl)methyl]phenol

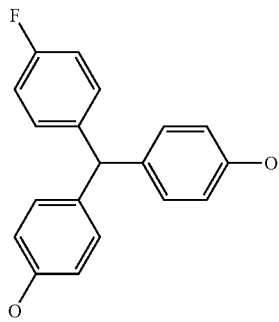 [SMILES: Oc1ccc(C(c2ccc(O)cc2)c2ccc(F)cc2)cc1]

Results Organization

Each query compound was searched against the CADD center up-to-date 5.04 million compound database using chemical fingerprint (BIT-MACCS) and physiochemical fingerprint (MPMFP). With chemical fingerprint, one may possibly identify structurally similar compounds with improved biological activity as well as start to obtain an idea of the relationship of the chemical structures to the function of the compounds. While with physiochemical fingerprints, the inventors can identify compounds with dissimilar structures but may still have activity allowing for the identification of novel lead compounds for future development.

The inventors use a similarity cutoff value to control the total number of similar compounds obtained from the similarity searches being located in 100-200 range which is a suitable size for sorting and ordering. See the following Table 1 for this information.

TABLE 1

| Compounds | Chemical | | Physiochemical | |
|---|---|---|---|---|
| | Sim % cutoff | Num of Sim Cmpds | Sim % cutoff | Num of Sim Cmpds |
| 5107930 (Compound 1) | 73.00% | 174 | 81.00% | 184 |
| 5100015 (Compound 2) | 60.00% | 154 | 83.00% | 141 |
| 1499-1221 (Compound 3) | 67.00% | 150 | 84.00% | 192 |
| 7771-0701 (Compound 4) | 72.00% | 160 | 79.00% | 119 |
| 0251-0215 (Compound 5) | 70.00% | 159 | 86.00% | 143 |

Example 4

As discussed above, the present inventors have identified Lipid II as a specific target for killing of Gram-positive bacteria by human defensins. A complex structure between HNP-1 and Lipid II was generated based on the partially solved crystal structure. The HNP-1-Lipid II binding site was identified and used for the design of compounds that mimic the binding of HNP-1 to Lipid II and thus serve as Lipid II-specific inhibitors. A similarity search in three large commercial chemical databases, Maybridge (Thermo Fisher Scientific Inc., Wattham, Mass.), ChemBridge (San Diego, Calif.), and ChemDiv (San Diego, Calif.), containing 59676, 482276, and 533143 compounds, respectively, identified ~100 compounds of interest, which may act as defensin-like molecules. Out of these ~100 compounds, the inventors selected the following for further antibacterial testing:

Chembridge: 6 compounds based on side-chain similarity,
13 compounds based on whole-chain similarity
ChemDiv: 5 compounds based on side-chain similarity,
8 compounds based on whole-chain similarity Based on the above, the inventors identified a lead compound with the following characteristics:
1) Effectively kills *S. aureus* at low concentrations
2) Shows little bactericidal activity against *E. coli*
3) Displays relatively low cytotoxicity Compound 1 (5107930)

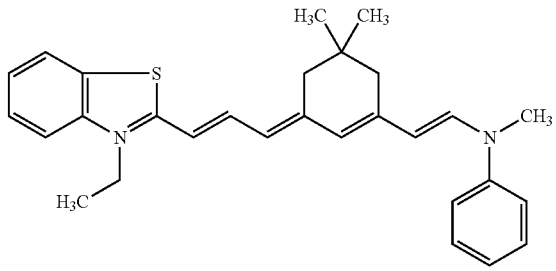

2-[3-(5,5-dimethyl-3-{2-[methyl(phenyl)amino]vinyl}-2-cyclohexen-1-ylidene)-1-propen-1-yl]-3-ethyl-1,3-benzothiazol-3-ium iodide Additional interesting compounds were identified, as discussed further below.

The inventors have now tested the bacterial killing capacity of the identified compounds. The antibacterial activity was determined using the vCC assay as discussed in Ericksen, B., Wu, Z., Lu, W. and Lehrer, R. I. (2005), "Antibacterial activity and specificity of the six human {alpha}-defensins. Antimicrob Agents" Chemother 49, 269-75.). All compounds were tested initially for killing of *Staphylococcus aureus* ATCC 29213. All compounds were dissolved in DiMethylSulfylOxide (DMSO) and exposed to bacteria for 30 minutes in concentrations ranging from 500 to 1.95 µM. Compounds effectively killing *S. aureus* were subsequently tested against *E. coli* ATCC 25922 to assay for strain-selectivity.

Figure 8:
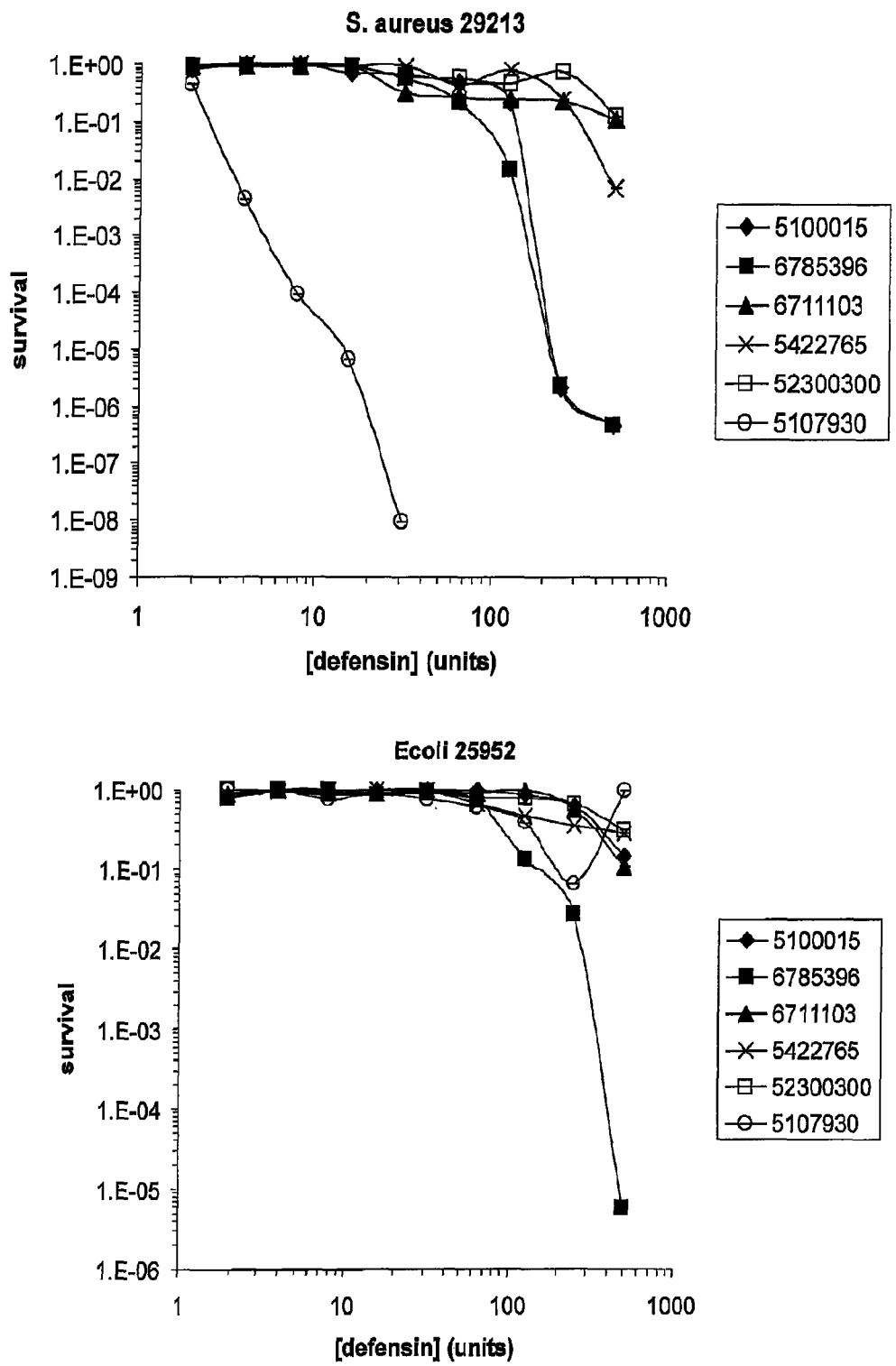
FIG. 8 depicts bacterial killing curves of select compounds that mimic Lipid II binding by HNP-1.

FIG. 8 depicts bacterial killing curves of select compounds that mimic Lipid II binding by HNP-1. All compounds were obtained from Chembridge Corporation.

Figure 9:
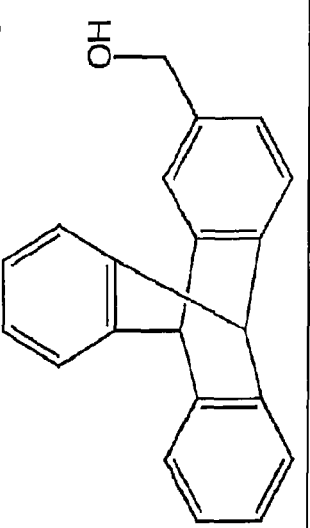
FIG. 9 depicts chemical structures of identified compounds, which were tested for use in accordance with the present invention.
Figure 9:
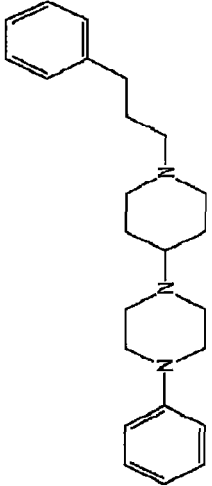
Figure 9:
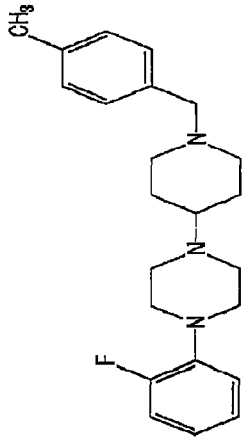

Chemical structures, ID number, Molecular Weight and Chemical Formula of Chembridge Corporation compounds are depicted in FIG. 9.

Figure 10:
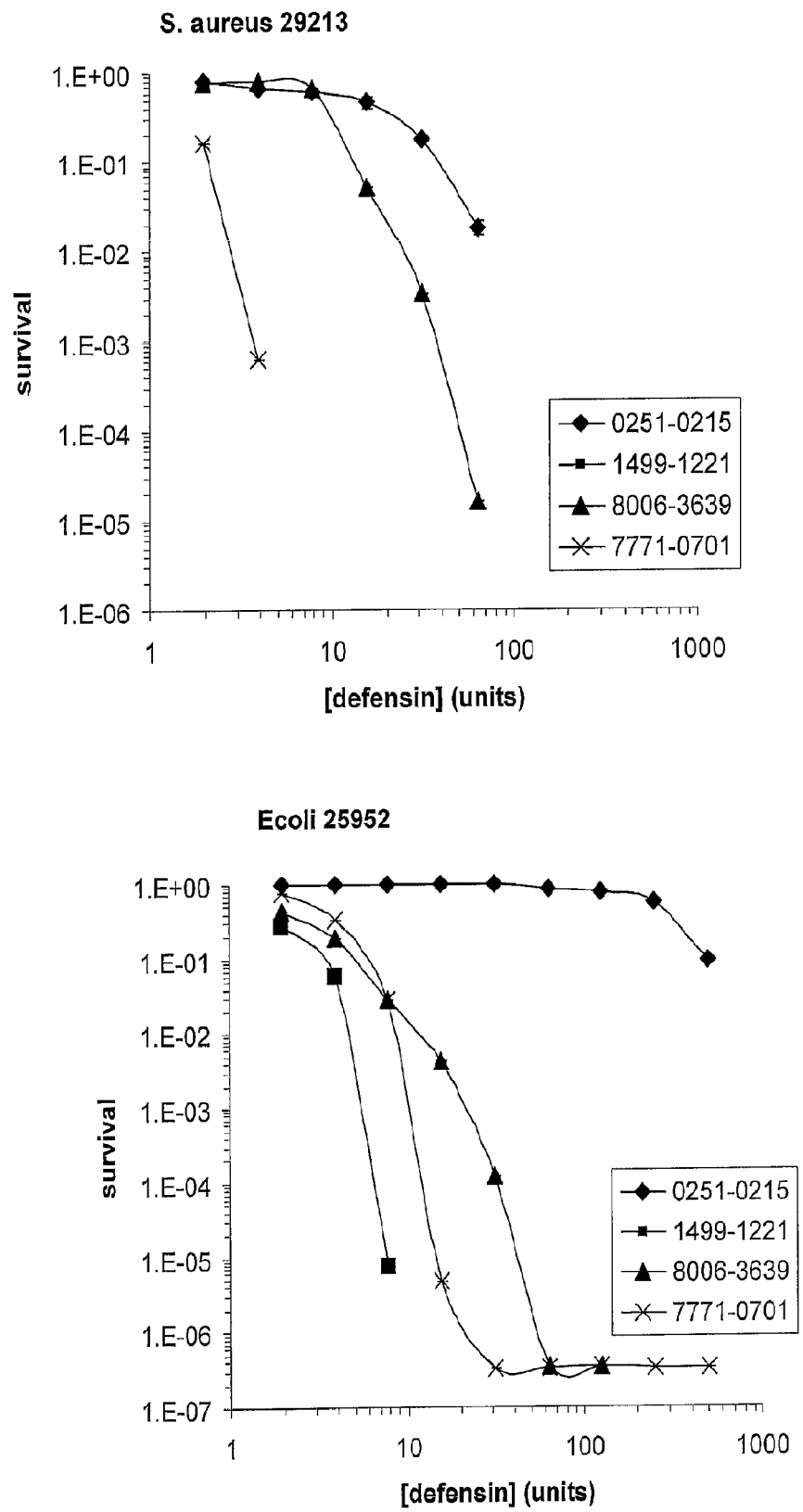
FIG. 10 depicts bacterial killing curves of select compounds that mimic Lipid II binding by HNP-1.

Bacterial killing curves of select compounds that mimic Lipid II binding by HNP-1 are depicted in FIG. 10. *NOTE: Compound 1499-1221 depicted in FIG. 10, resulted in complete killing of *S. aureus*. Because datapoints are plotted only when bacterial growth has occurred, there are no points at this concentration range for this compound. It is demonstrated in FIG. 10.

Figure 11:
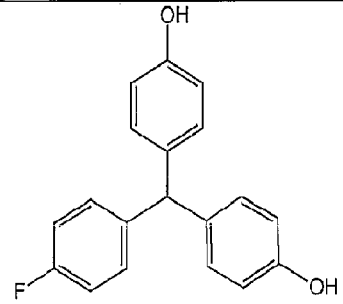
FIG. 11 depicts chemical structures, ID number, Molecular Weight and Chemical Formula of ChemDiv Corporation compounds tested for possible use with the present methods.
Figure 11:
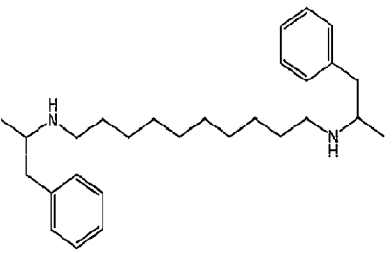
Figure 11:
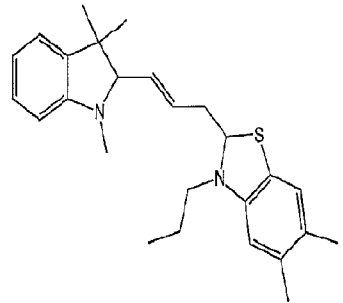
Figure 11:
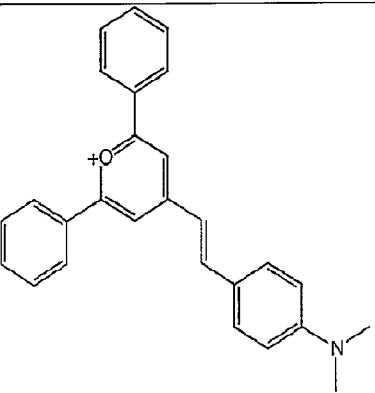

FIG. 11 depicts the Chemical structures, ID number, Molecular Weight and Chemical Formula of ChemDiv Corporation compounds.

Figure 12:
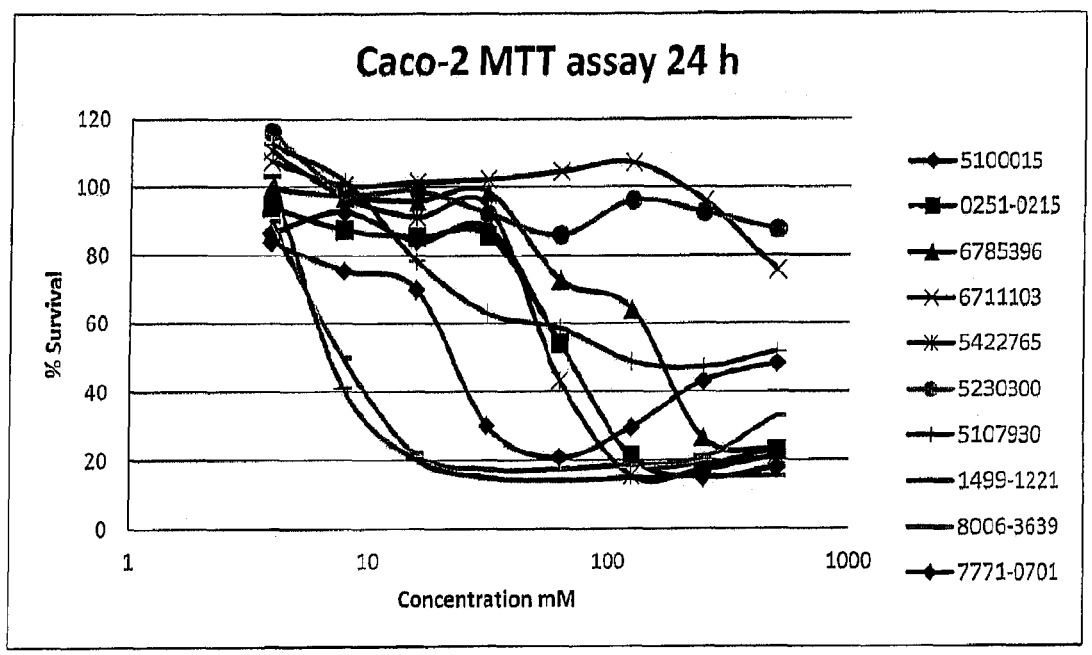
FIG. 12 demonstrates the effect of selected compounds on the cell viability of the intestinal epithelial cell line Caco-2. Caco-2.

FIG. 12 demonstrates the effect of selected compounds on the cell viability of the intestinal epithelial cell line Caco-2. Caco-2 cells were seeded at 2. 105 cells/ml and exposed to compounds ranging in concentration from 500 to 3.7125 µM. Cell viability was determined after 24 h by the MTT assay and is expressed as a percentage of the viability of untreated cells.

Although the invention has been described in example embodiments, those skilled in the art will appreciate that various modifications may be made without departing from the spirit and scope of the invention. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

What is claimed is:

1. A method of treating infections in mammals caused by microorganisms, comprising administering to a mammal a therapeutically effective amount of
2-[(E)-2-[4-(dimethylamino)phenyl]ethenyl]-4,6-diphenyl-pyran-3-ylium

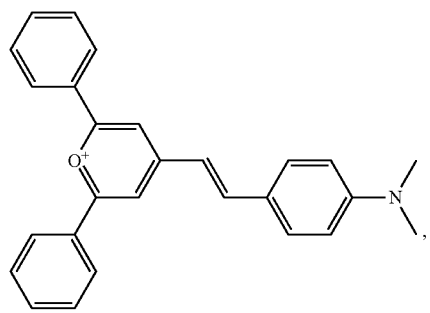 [SMILES: CN(C)c1ccc(/C=C/c2cc(-c3ccccc3)[o+]c(-c3ccccc3)c2)cc1]

wherein said microorganisms comprise one or more gram-positive bacteria selected from the group consisting of *Staphylococcus*, *Streptococcus*, and *Enterococcus*.

2. The method of claim 1, wherein said microorganisms comprise one or more gram-positive bacteria selected from the group consisting of *Staphylococcus aureus*, *Streptococcus pyogenes*, *Streptococcus agalactiae*, *Streptococcus anginosus* group, and *Enterococcus faecalis*.

3. The method of claim 1, wherein the 2-[(E)-2-[4-(dimethylamino)phenyl]ethenyl]-4,6-diphenyl-pyran-3-ylium is administered to the mammal as part of a composition.

4. A method of killing a bacterial population in a mammal comprising administering to a mammal a therapeutically effective amount for killing the bacterial population in the mammal, of:
2-[(E)-2-[4-(dimethylamino)phenyl]ethenyl]-4,6-diphenyl-pyran-3-ylium

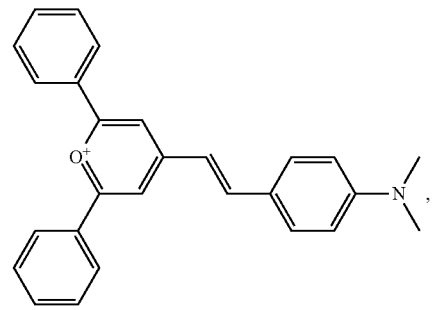 [SMILES: CN(C)c1ccc(/C=C/c2cc(-c3ccccc3)[o+]c(-c3ccccc3)c2)cc1]

wherein said bacterial population comprises a population of one or more gram-positive bacteria selected from the group consisting of *Staphylococcus*, *Streptococcus*, and *Enterococcus*.

5. The method of claim 4, wherein the 2-[(E)-2-[4-(dimethylamino)phenyl]ethenyl]-4,6-diphenyl-pyran-3-ylium is administered to the mammal as part of a composition.

6. The method of claim 4, wherein said bacterial population comprises a population of one or more gram-positive bacteria selected from the group consisting of *Staphylococcus aureus*, *Streptococcus pyogenes*, *Streptococcus agalactiae*, *Streptococcus anginosus* group, and *Enterococcus faecalis*.

* * * * *